US011129681B2

United States Patent
Amiot et al.

(10) Patent No.: US 11,129,681 B2
(45) Date of Patent: Sep. 28, 2021

(54) BONE AND TOOL TRACKING IN ROBOTIZED COMPUTER-ASSISTED SURGERY

(71) Applicant: ORTHOSOFT INC., Montreal (CA)

(72) Inventors: Louis-Philippe Amiot, Montreal (CA); Pierre Couture, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 658 days.

(21) Appl. No.: 15/902,420

(22) Filed: Feb. 22, 2018

(65) Prior Publication Data

US 2018/0235715 A1 Aug. 23, 2018

Related U.S. Application Data

(60) Provisional application No. 62/529,745, filed on Jul. 7, 2017, provisional application No. 62/461,995, filed on Feb. 22, 2017.

(51) Int. Cl.
*A61B 34/10* (2016.01)
*A61B 34/20* (2016.01)
(Continued)

(52) U.S. Cl.
CPC .............. *A61B 34/20* (2016.02); *A61B 34/10* (2016.02); *G01B 11/25* (2013.01); *G16H 40/60* (2018.01);
(Continued)

(58) Field of Classification Search
CPC . A61B 34/20; A61B 34/10; A61B 2034/2057; A61B 2034/2065;
(Continued)

(56) References Cited

U.S. PATENT DOCUMENTS 8,160,345 B2 * 4/2012 Pavlovskaia ........... A61B 5/055
 382/131
8,311,306 B2 * 11/2012 Pavlovskaia ......... A61B 17/157
 382/131
(Continued)

FOREIGN PATENT DOCUMENTS

WO 2016114834 A2 7/2016
WO 2017011576 A2 1/2017

*Primary Examiner* — Sanjay Cattungal
(74) *Attorney, Agent, or Firm* — Norton Rose Fulbright Canada LLP

(57) ABSTRACT

A system for tracking at least one bone in robotized computer-assisted surgery, comprises a processing unit and a non-transitory computer-readable memory communicatively coupled to the processing unit and comprising computer-readable program instructions executable by the processing unit for: obtaining backscatter images of the at least one bone from a tracking device in a coordinate system; generating a three-dimensional geometry of a surface of the at least one bone from the backscatter images, the three-dimensional geometry of the surface being in the coordinate system; determining a position and orientation of the at least one bone in the coordinate system by matching the three-dimensional geometry of the surface of the at least one bone to a three-dimensional model of the bone; controlling an automated robotized variation of at least one of a position and orientation of the tracking device as a function of a processing of the backscatter images; and continuously outputting the position and orientation of the at least one bone in the coordinate system to a robot driver controlling a robot arm supporting a surgical tool in the coordinate system for altering the bone.

18 Claims, 4 Drawing Sheets

(51) Int. Cl.
*G16H 40/60* (2018.01)
*G01B 11/25* (2006.01)
*A61B 34/30* (2016.01)
*A61B 90/00* (2016.01)
*A61B 90/96* (2016.01)

(52) U.S. Cl.
CPC .............. *A61B 34/30* (2016.02); *A61B 90/96* (2016.02); *A61B 2034/105* (2016.02); *A61B 2034/2048* (2016.02); *A61B 2034/2051* (2016.02); *A61B 2034/2055* (2016.02); *A61B 2034/2057* (2016.02); *A61B 2034/2059* (2016.02); *A61B 2034/2063* (2016.02); *A61B 2034/2065* (2016.02); *A61B 2090/371* (2016.02); *A61B 2090/373* (2016.02)

(58) Field of Classification Search
CPC ...... A61B 2034/2048; A61B 2090/373; A61B 2034/2059; A61B 90/96; A61B 2090/371; A61B 34/30; A61B 2034/105; A61B 2034/2055; A61B 2034/2063; A61B 2034/2051; G01B 11/25; G16H 40/60
See application file for complete search history.

(56) References Cited

U.S. PATENT DOCUMENTS

| | | | |
|---|---|---|---|
| 8,545,509 B2* | 10/2013 | Park | A61B 5/4533 606/88 |
| 8,737,700 B2* | 5/2014 | Park | B33Y 50/00 382/128 |
| 9,498,231 B2* | 11/2016 | Haider | A61B 34/37 |
| 9,730,713 B2* | 8/2017 | Park | A61B 17/171 |
| 2007/0219561 A1* | 9/2007 | Lavallee | A61B 34/20 606/90 |
| 2008/0119719 A1* | 5/2008 | Ascenzi | G06T 7/0012 600/410 |
| 2008/0253511 A1* | 10/2008 | Boyden | G01N 23/201 378/21 |
| 2008/0253520 A1* | 10/2008 | Boyden | G01N 23/201 378/86 |
| 2008/0253522 A1* | 10/2008 | Boyden | G01N 23/201 378/87 |
| 2008/0253527 A1* | 10/2008 | Boyden | A61B 6/145 378/87 |
| 2008/0253637 A1* | 10/2008 | Boyden | A61B 6/483 382/131 |
| 2009/0296887 A1* | 12/2009 | Boyden | G01T 1/161 378/87 |
| 2010/0274389 A1 | 10/2010 | Ortmaier et al. | |
| 2011/0029093 A1* | 2/2011 | Bojarski | A61F 2/389 623/20.35 |
| 2011/0130761 A1* | 6/2011 | Plaskos | A61B 34/30 606/87 |
| 2011/0196376 A1* | 8/2011 | Ozgur | A61B 34/20 606/80 |
| 2011/0251625 A1 | 10/2011 | Bulitta et al. | |
| 2011/0295378 A1* | 12/2011 | Bojarski | A61F 2/30 623/20.35 |
| 2012/0157829 A1* | 6/2012 | Boyden | A61B 6/4021 600/427 |
| 2012/0157830 A1* | 6/2012 | Boyden | A61B 6/505 600/427 |
| 2012/0209394 A1* | 8/2012 | Bojarski | A61B 17/157 623/20.32 |
| 2013/0096373 A1* | 4/2013 | Chabanas | G06T 7/75 600/101 |
| 2013/0211531 A1* | 8/2013 | Steines | A61F 2/3859 623/20.35 |
| 2014/0188129 A1 | 3/2014 | Kang | |
| 2014/0228860 A1* | 8/2014 | Steines | A61B 34/30 606/130 |
| 2016/0106554 A1* | 4/2016 | Lavallee | A61B 17/154 606/102 |
| 2016/0166333 A1 | 6/2016 | Wang et al. | |
| 2016/0191887 A1* | 6/2016 | Casas | H04N 13/156 348/47 |
| 2017/0258526 A1* | 9/2017 | Lang | A61B 17/1703 |
| 2017/0340389 A1* | 11/2017 | Otto | A61B 34/10 |
| 2017/0360512 A1* | 12/2017 | Couture | A61B 17/1675 |
| 2018/0021097 A1* | 1/2018 | Quaid | A61B 17/1764 606/130 |
| 2018/0132949 A1* | 5/2018 | Merette | G06T 11/60 |
| 2018/0199995 A1* | 7/2018 | Odermatt | A61B 5/107 |
| 2019/0142524 A1 | 5/2019 | Hladio et al. | |
| 2019/0201155 A1* | 7/2019 | Gupta | A61B 5/055 |

* cited by examiner

BONE AND TOOL TRACKING IN ROBOTIZED COMPUTER-ASSISTED SURGERY

CROSS-REFERENCE TO RELATED APPLICATION

The present application claims the priority of U.S. Patent Application Ser. No. 62/461,995, filed on Feb. 22, 2017, and the priority of U.S. Patent Application Ser. No. 62/529,745, filed on Jul. 7, 2017, both of which are included herein by reference.

TECHNICAL FIELD

The present application relates to bone and tool tracking in computer-assisted orthopedic surgery and in robotized computer-assisted surgery.

BACKGROUND OF THE ART

Tracking of surgical instruments or tools is an integral part of computer-assisted surgery (hereinafter "CAS"). The tools are tracked for position and/or orientation in such a way that information pertaining to bodily parts is obtained. The information is then used in various interventions (e.g., orthopedic surgery, neurological surgery) with respect to the body, such as bone alterations, implant positioning, incisions and the like during surgery.

The tracking technologies may use different technologies, such as mechanical, acoustical, magnetic, optical and radio frequency (RF) tracking. Depending on the technology used, different types of trackable members are fixed, permanently or temporarily, to the item that needs to be tracked. For instance, during Total Knee Replacement (TKR) surgery, trackable members are fixed to the limbs and to the different surgical instruments, and these trackable members are tracked by the tracking system. The CAS system calculates position and orientation data associated with the tracking, and the information displayed by the computer is used by the surgeon to visualize the position of the instrument(s) being manipulated with respect to the limbs, or in numerical values.

Optical tracking is commonly used in different forms. For example, passive retroreflective components are provided on tools and bones. In order to obtain values for position and/or orientation, the optical elements must be in the line of sight of the optical sensor device. As other examples, structured light tracking and laser rangefinder tracking are known optical tracking technologies. One common constraint with optical tracking systems is the requirement for a line of sight between image acquisition devices and the objects to track. Accordingly, surgery employing optical tracking may be imposed a given orientation as a function of the required visibility between the optical sensor apparatus and the optical elements. If the line of sight is disrupted, orthopedic tracking may be paused, as a possible consequence. In automated robotic surgery, the interruption of optical tracking may result in the need for human intervention. There remains room for improvement.

SUMMARY

In accordance with a first embodiment of the present disclosure, there is provided a system for tracking at least one bone in robotized computer-assisted surgery, comprising: a processing unit; and a non-transitory computer-readable memory communicatively coupled to the processing unit and comprising computer-readable program instructions executable by the processing unit for: obtaining backscatter images of the at least one bone from a tracking device in a coordinate system; generating a three-dimensional geometry of a surface of the at least one bone from the backscatter images, the three-dimensional geometry of the surface being in the coordinate system; determining a position and orientation of the at least one bone in the coordinate system by matching the three-dimensional geometry of the surface of the at least one bone to a three-dimensional model of the bone; controlling an automated robotized variation of at least one of a position and orientation of the tracking device as a function of a processing of the backscatter images; and continuously outputting the position and orientation of the at least one bone in the coordinate system to a robot driver controlling a robot arm supporting a surgical tool in the coordinate system for altering the bone.

Further in accordance with the first embodiment, controlling the automated robotized variation comprises for example identifying an image ratio of the at least one bone relative to environment in the backscatter images and controlling the automated robotized variation to increase the image ratio.

Still further in accordance with the first embodiment, controlling the automated robotized variation comprises for example creating field of view data indicative of the orientation of the at least one bone relative to the position and orientation of the tracking device, and selecting the position and orientation of the tracking device as a function of a desired point of view of the at least bone.

Still further in accordance with the first embodiment, selecting the position and orientation of the tracking device as a function of a desired point of view of the at least bone includes for example determining an upcoming location of the surgical tool on the robot arm from a surgical flow of surgery planning.

Still further in accordance with the first embodiment, obtaining backscatter images of the at least one bone from the tracking device in the coordinate system comprises for example obtaining backscatter images of the surgical tool; and generating the three-dimensional geometry of the surface of the at least one bone from the backscatter images comprises for example generating a three-dimensional geometry of a surface of the surgical tool from the backscatter images in the coordinate system.

Still further in accordance with the first embodiment, continuously outputting the position and orientation of the at least one bone in the coordinate system includes for example continuously outputting the position and orientation of the surgical tool to the robot driver controlling the robot arm supporting the surgical tool in the coordinate system.

Still further in accordance with the first embodiment, the position and orientation of the surgical tool obtained from the backscatter images is verified for example with a position and orientation of the surgical tool provided by the robot driver and outputting a discrepancy.

Still further in accordance with the first embodiment, determining the position and orientation of the at least one bone in the coordinate system includes for example determining the position and orientation of the surgical tool in the coordinate system by matching the three-dimensional geometry of the surface of the surgical tool to a three-dimensional model of the surgical tool.

Still further in accordance with the first embodiment, obtaining backscatter images of the at least one bone from a tracking device in a coordinate system includes for example obtaining the backscatter images in a low-frequency capture mode when the surgical tool is distal to the bone, and in a high-frequency capture mode when the surgical tool is proximal to the bone.

Still further in accordance with the first embodiment, obtaining the backscatter images in the low-frequency capture mode or the high-frequency capture mode includes for example determining an upcoming location of the surgical tool on the robot arm from a surgical flow of surgery planning.

Still further in accordance with the first embodiment, obtaining the backscatter images of the at least one bone includes for example obtaining the backscatter images from a point of view on a tool interfacing with an anatomical part surrounding the bone or with the bone.

Still further in accordance with the first embodiment, controlling the automated robotized variation of at least one of the position and orientation of the tracking device includes for example controlling a robotized tracker arm of the tracking device.

Still further in accordance with the first embodiment, generating the three-dimensional geometry of the surface of the at least one bone from the backscatter images includes for example generating an altered surface, and wherein determining the position and orientation of the at least one bone in the coordinate system includes determining the position and orientation of the altered surface in the bone.

Still further in accordance with the first embodiment, the position and orientation of altered surface is verified for example with a position and orientation of a planned altered surface from surgery planning and outputting a discrepancy.

Still further in accordance with the first embodiment, an interference from the backscatter images of the at least one bone is identified for example and an indication of interference is output for example.

Still further in accordance with the first embodiment, obtaining the backscatter images includes for example obtaining the backscatter images from visible structured light.

In accordance with a second embodiment of the present disclosure, there is provided a system for tracking at least one bone in robotized computer-assisted surgery, comprising: a tracking device including at least a structured light source and a camera to generate and obtain the backscatter images; and a computer-assisted surgery controller for obtaining backscatter images of the at least one bone from the tracking device in a coordinate system, generating a three-dimensional geometry of a surface of the at least one bone from the backscatter images, the three-dimensional geometry of the surface being in the coordinate system, determining a position and orientation of the at least one bone in the coordinate system by matching the three-dimensional geometry of the surface of the at least one bone to a three-dimensional model of the bone, controlling an automated robotized variation of at least one of a position and orientation of the tracking device as a function of a processing of the backscatter images, and continuously outputting the position and orientation of the at least one bone in the coordinate system to a robot driver controlling a robot arm supporting a surgical tool in the coordinate system for altering the bone.

Further in accordance with the second embodiment, the computer-assisted surgery controller includes for example a position optimizer module for identifying an image ratio of the at least one bone relative to environment in the backscatter images, for controlling the automated robotized variation to increase the image ratio.

Still further in accordance with the second embodiment, further comprising a field of view navigator module creates for example field of view data indicative of the orientation of the at least one bone relative to the position and orientation of the tracking device, and selects for example the position and orientation of the tracking device as a function of a desired point of view of the at least bone.

Still further in accordance with the second embodiment, the field of view navigator module selects for example the position and orientation of the tracking device by determining an upcoming location of the surgical tool on the robot arm from a surgical flow of surgery planning.

Still further in accordance with the second embodiment, obtaining backscatter images of the at least one bone from the tracking device in the coordinate system comprises for example obtaining backscatter images of the surgical tool, and generating the three-dimensional geometry of the surface of the at least one bone from the backscatter images comprises generating a three-dimensional geometry of a surface of the surgical tool from the backscatter images in the coordinate system.

Still further in accordance with the second embodiment, continuously outputting the position and orientation of the at least one bone in the coordinate system includes for example continuously outputting the position and orientation of the surgical tool to the robot driver controlling the robot arm supporting the surgical tool in the coordinate system.

Still further in accordance with the second embodiment, the position and orientation of the surgical tool obtained from the backscatter images is verified for example with a position and orientation of the surgical tool provided by the robot driver and outputting a discrepancy.

Still further in accordance with the second embodiment, determining the position and orientation of the at least one bone in the coordinate system includes for example determining the position and orientation of the surgical tool in the coordinate system by matching the three-dimensional geometry of the surface of the surgical tool to a three-dimensional model of the surgical tool.

Still further in accordance with the second embodiment, obtaining backscatter images of the at least one bone from the tracking device in the coordinate system includes for example operating the tracking device in a low-frequency capture mode when the surgical tool is distal to the bone, and in a high-frequency capture mode when the surgical tool is proximal to the bone.

Still further in accordance with the second embodiment, operating the tracking device in the low-frequency capture mode or the high-frequency capture mode includes for example determining an upcoming location of the surgical tool on the robot arm from a surgical flow of surgery planning.

Still further in accordance with the second embodiment, the camera of the tracking device is located for example on a tool adapted to interface with an anatomical part surrounding the bone or with the bone.

Still further in accordance with the second embodiment, generating the three-dimensional geometry of the surface of the at least one bone from the backscatter images includes for example generating an altered surface, and wherein determining the position and orientation of the at least one bone in the coordinate system includes for example determining the position and orientation of the altered surface in the bone.

Still further in accordance with the second embodiment, the position and orientation of altered surface is verified for example with a position and orientation of a planned altered surface from surgery planning and outputting a discrepancy.

Still further in accordance with the second embodiment, a robotized tracker arm supports for example the tracking device, and wherein the computer-assisted surgery controller includes for example the robot driver for controlling the robotized tracker arm, whereby controlling the automated robotized variation of at least one of the position and orientation of the tracking device includes controlling the robotized tracker arm of the tracking device.

Still further in accordance with the second embodiment, the computer-assisted surgery controller includes for example an interference identifier module for identifying an interference from the backscatter images of the at least one bone, whereby the computer-assisted surgery controller outputs an indication of interference.

Still further in accordance with the second embodiment, the structured light source produces for example structured light at least in a visible light spectrum.

In accordance with a third embodiment of the present disclosure, there is provided a method for tracking at least one bone in computer-assisted surgery, comprising: obtaining backscatter images of the at least one bone from a tracking device in a coordinate system, as positioned on a tool interfacing with an anatomical part surrounding the bone or with the bone; generating a three-dimensional geometry of a surface of the at least one bone from the backscatter images, the three-dimensional geometry of the surface being in the coordinate system; determining a position and orientation of the at least one bone in the coordinate system by matching the three-dimensional geometry of the surface of the at least one bone to a three-dimensional model of the bone; and continuously outputting the position and orientation of the at least one bone in the coordinate system to an interface for providing guidance in altering the bone.

Further in accordance with the third embodiment, obtaining backscatter images of the at least one bone from the tracking device in the coordinate system comprises for example obtaining backscatter images of the surgical tool, and generating the three-dimensional geometry of the surface of the at least one bone from the backscatter images comprises for example generating a three-dimensional geometry of a surface of the surgical tool from the backscatter images in the coordinate system.

Still further in accordance with the third embodiment, continuously outputting the position and orientation of the at least one bone in the coordinate system includes for example continuously outputting the position and orientation of the surgical tool in the coordinate system.

Still further in accordance with the third embodiment, determining the position and orientation of the at least one bone in the coordinate system includes for example determining the position and orientation of the surgical tool in the coordinate system by matching the three-dimensional geometry of the surface of the surgical tool to a three-dimensional model of the surgical tool.

Still further in accordance with the third embodiment, obtaining backscatter images of the at least one bone from a tracking device in a coordinate system includes for example obtaining the backscatter images in a low-frequency capture mode when the surgical tool is distal to the bone, and in a high-frequency capture mode when the surgical tool is proximal to the bone.

Still further in accordance with the third embodiment, obtaining the backscatter images in the low-frequency capture mode or the high-frequency capture mode includes for example determining an upcoming location of the surgical tool from a surgical flow of surgery planning.

Still further in accordance with the third embodiment, generating the three-dimensional geometry of the surface of the at least one bone from the backscatter images includes for example generating an altered surface, and wherein determining the position and orientation of the at least one bone in the coordinate system includes for example determining the position and orientation of the altered surface in the bone.

Still further in accordance with the third embodiment, an automated robotized variation of at least one of a position and orientation of the tracking device is controlled for example as a function of a processing of the backscatter images, and the position and orientation of the at least one bone in the coordinate system is continuously output for example to a robot driver controlling a robot arm supporting a surgical tool in the coordinate system for altering the bone.

Still further in accordance with the third embodiment, controlling the automated robotized variation comprises for example identifying an image ratio of the at least one bone relative to environment in the backscatter images and controlling the automated robotized variation to increase the image ratio.

Still further in accordance with the third embodiment, controlling the automated robotized variation comprises for example creating field of view data indicative of the orientation of the at least one bone relative to the position and orientation of the tracking device, and selecting the position and orientation of the tracking device as a function of a desired point of view of the at least bone.

Still further in accordance with the third embodiment, selecting the position and orientation of the tracking device as a function of a desired point of view of the at least bone includes for example determining an upcoming location of the surgical tool on the robot arm from a surgical flow of surgery planning.

Still further in accordance with the third embodiment, the position and orientation of the surgical tool obtained from the backscatter images is verified for example with a position and orientation of the surgical tool provided by the robot driver and outputting a discrepancy.

Still further in accordance with the third embodiment, controlling the automated robotized variation of at least one of the position and orientation of the tracking device includes for example controlling a robotized tracker arm of the tracking device.

Still further in accordance with the third embodiment, obtaining the backscatter images includes for example obtaining the backscatter images from visible structured light.

In accordance with a fourth embodiment of the present disclosure, there is provided a system for tracking at least one bone in robotized computer-assisted surgery, comprising: a processing unit; and a non-transitory computer-readable memory communicatively coupled to the processing unit and comprising computer-readable program instructions executable by the processing unit for: obtaining images of the at least one bone from a tracking device in a coordinate system, with at least one patch on the bone, the patch having a trackable pattern thereon; associating a three-dimensional geometry of a surface of the at least one bone to the patch, the three-dimensional geometry of the surface being in the coordinate system; determining a position and orientation of the at least one bone in the coordinate system by matching the three-dimensional geometry of the surface of the at least one bone to a three-dimensional model of the bone; controlling an automated robotized variation of at least one of a position and orientation of the tracking device as a function of a processing of the images; and continuously outputting the position and orientation of the at least one bone in the coordinate system to a robot driver controlling a robot arm supporting a surgical tool in the coordinate system for altering the bone.

DETAILED DESCRIPTION

Figure 1:
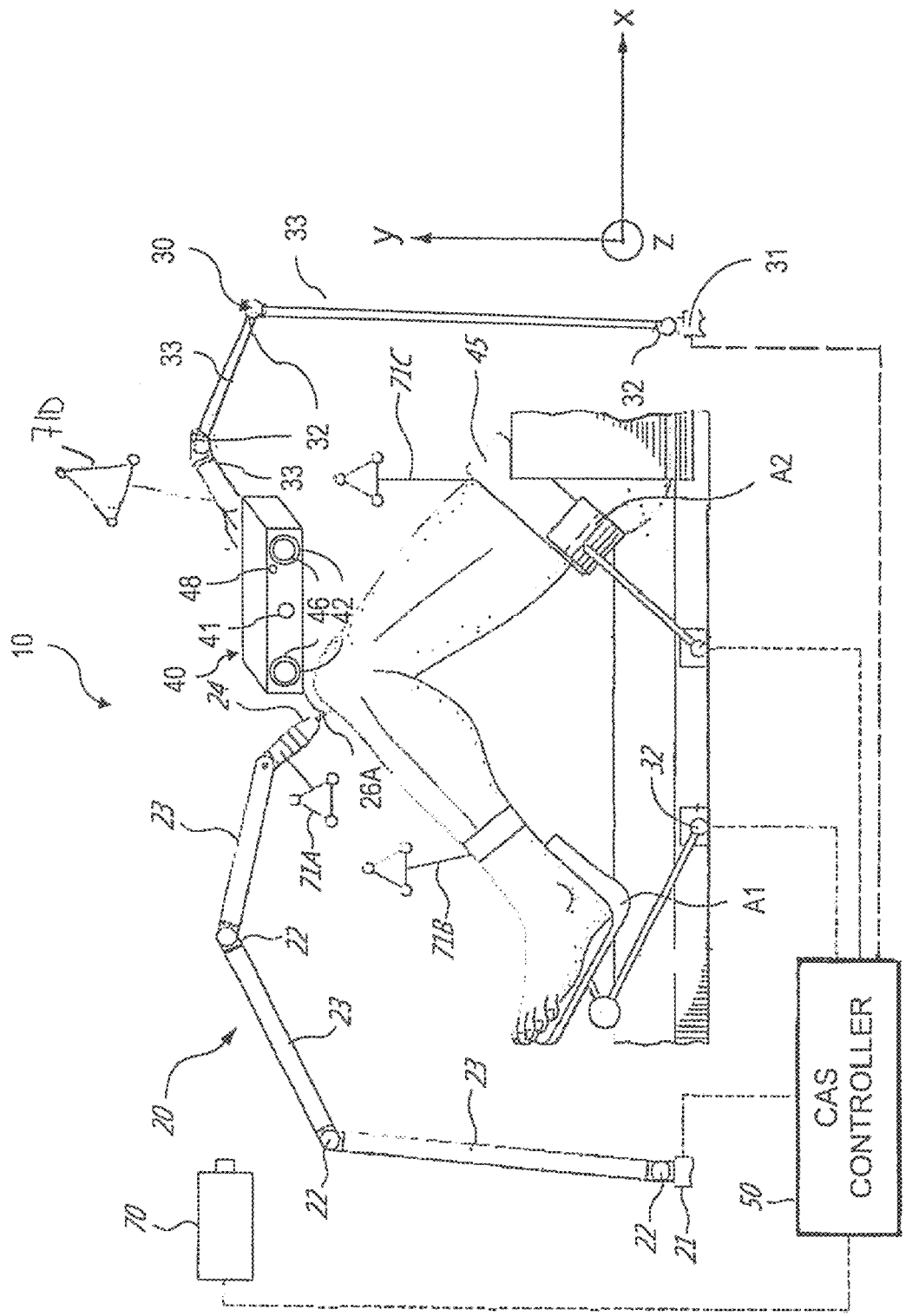
FIG. 1 is a schematic view of an automated robotic computer-assisted surgery (CAS) system in accordance with the present disclosure.

Referring to the drawings and more particularly to FIG. 1, an automated robotic computer-assisted surgery (CAS) system is generally shown at 10, and is used to perform orthopedic surgery maneuvers on a patient, including pre-operative analysis of range of motion and implant assessment planning, as described hereinafter. The system 10 is shown relative to a patient's knee joint in supine decubitus, but only as an example. The system 10 could be used for other body parts, including non-exhaustively hip joint, spine, and shoulder bones.

The CAS system 10 is robotized, and has or may have a robot arm 20, a tracker arm 30, a tracking device 40, a CAS controller 50, a tracking controller 60 (FIG. 2), and a secondary tracking device 70:

The robot arm 20 is the working end of the system 10, and is used to perform bone alterations as planned by an operator and/or the CAS controller 50 and as controlled by the CAS controller 50. The robot arm 20 may also be configured for collaborative/cooperative mode in which the operator may manipulate the robot arm 20. For example, the tooling end, also known as end effector, may be manipulated by the operator;

The tracker arm 30 supports the tracking device 40. The tracker arm 30 is robotized in that its movements can be controlled by the CAS controller 50;

The tracking device 40 performs image acquisition in optical tracking, using for instance structured light, or three-dimensional (3D) camera tracking, also known as range imaging, depth imaging, in contrast to structured light tracking with structured light pattern projection;

The CAS controller 50 controls the robot arm 20 and the tracker arm 30, and operates the tracking device 40. Moreover, as described hereinafter, the CAS controller 50 may also drive the robot arm 20 through a planned surgical procedure;

The tracking controller 60 is tasked with determining the position and/or orientation of the various relevant objects during the surgery procedure, such as the bone(s) and tool(s), using data acquired by the tracking device 40. The position and/or orientation is used by the CAS controller 50 to control the robot arm 20 and the tracker arm 30.

The secondary tracking device 70 may optionally be used to track the bones of the patient, and the robot arm 20. For example, the secondary tracking device 70 may assist in performing the calibration of the patient bone with respect to the robot arm 20, i.e. determining its position and orientation, for subsequent navigation in a coordinate system (also known as frame of reference, global reference system, etc).

Referring to FIG. 1, a schematic example of the robot arm 20 and of the tracker arm 30 is provided. The robot arm 20 may stand from a base 21, for instance in a fixed relation relative to the operating-room (OR) table supporting the patient, whether it is attached or detached from the table. The relative positioning of the robot arm 20 relative to the patient is a determinative factor in the precision of the surgical procedure, whereby a foot support A1 and thigh support A2 may assist in keeping the operated limb fixed in the illustrated X, Y, Z coordinate system. Although not shown, the foot support A1 and/or the thigh support A2 could be automated to robotize the displacement and positioning of the patient's leg, and optionally to perform tests on the leg. The robot arm 20 has a plurality of joints 22 and links 23, of any appropriate form, to support a tool head 24 that interfaces with the patient. For example, the end effector or tool head 24 may optionally incorporate a force/torque sensor for collaborative/cooperative control mode, in which an operator manipulates the robot arm 20. The robot arm 20 is shown being a serial mechanism, arranged for the tool head 24 to be displaceable in a desired number of degrees of freedom (DOF). For example, the robot arm 20 controls 6-DOF movements of the tool head 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the tool head 24 in the manner described above. The joints 22 are powered for the robot arm 20 to move as controlled by the CAS controller 50 in the six DOFs, and in such a way that the position and orientation of the tool head 24 in the coordinate system may be known, for instance by readings from encoders on the various joints 22. Therefore, the powering of the joints 22 is such that the tool head 24 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, and incorporated herein by reference. The position and orientation of the tool head 24 may be calculated using solely the encoders on the various joints. The tracking device 40 and/or secondary tracking device 70 may also be used for this purpose, or other systems such as inertial sensor systems. It may be necessary to have the base 21 of the robot arm 20 fixed in a known location relative to the tracker arm 30 or alternatively be marked with a tracking pattern compatible with the secondary tracking device 70.

In FIG. 1, the tool head 24 supports a burr 26A, used to resurface or drill a bone. The tool head 24 may also comprise a chuck or like tool interface, typically actuatable in rotation. The tool head 24 may have laminar spreader plates, actuatable independently from a remainder of the tool head 24, for simultaneous use with a tool support by the tool head 24. The laminar spreader plates are used to spread soft tissue apart to expose the operation site. The laminar spreader plates may also be used as pincers, to grasp objects, etc. As a non-exhaustive example, other tools that may be supported by the tool head 24 include a registration pointer, a reamer (e.g., cylindrical, tapered), a reciprocating saw, a retractor, a laser rangefinder or light-emitting device (e.g., the indicator device of U.S. Pat. No. 8,882,777) depending on the nature of the surgery. The various tools may be part of a multi-mandible configuration or may be interchangeable, whether with human assistance, or as an automated process. The installation of a tool in the tool head 24 may then require some calibration in order to track the installed tool in the X, Y, Z coordinate system of the robot arm 20.

The tracker arm 30 may also stand from a base 31, for instance in a fixed relation relative to the operating-room (OR) table supporting the patient of the base 21 of the robot arm 20. The relative positioning of the tracker arm 30 relative to the patient is adjustable as described below to ensure that the resected bone portion is tracked in the illustrated X, Y, Z coordinate system, relative to the tool head 24. The tracker arm 30 has a plurality of joints 32 and links 33, of any appropriate form, to support the tracking device 40. The tracker arm 30 is shown being a serial mechanism, arranged for the tracking device 40 to be displaceable in a desired number of degrees of freedom (DOF). For example, the tracker arm 30 controls 6-DOF movements of the tracking device 40, i.e., X, Y, Z in the coordinate system, and pitch, roll and yaw. Fewer or additional DOFs may be present. For simplicity, only a generic illustration of the joints 32 and links 33 is provided, but more joints of different types may be present to move the tracking device 40 in the manner described above. The joints 32 are powered for the tracker arm 30 to move as controlled by the CAS controller 50 in the six DOFs, and in such a way that the position and orientation of the tracking device 40 may be known, for instance by readings from encoders on the various joints 32. Therefore, the powering of the joints 32 is such that the tracking device 40 at the end of the tracker arm 30 may execute precise movements. The tracker arm 30 may be similar to robot arms as described in U.S. patent application Ser. No. 11/610,728.

The tracking device 40 is mounted to the end of the tracker arm 30. The tracking device 40 is of the type using light backscatter (a.k.a. backscattered radiation) to surgically track objects. In the present disclosure, the tracking device 40 may be used to track tools and bones so as to guide the robot arm 20 in altering the bone based on surgery planning. Backscattered radiation can be used for acquisition of 3D surface geometries of bones and tools.

The tracking device 40 may produce structured light illumination for tracking objects with structured light 3D imaging. In structured light illumination, a portion of the objects is illuminated with one or multiple patterns from a pattern projector 41. Structured light 3D imaging is based on the fact that a projection of a line of light from the pattern projector 41 onto a 3D shaped surface produces a line of illumination that appears distorted as viewed from perspectives other than that of the pattern projector 41. Accordingly, imaging such a distorted line of illumination allows a geometric reconstruction of the 3D shaped surface. Imaging of the distorted line of illumination is generally performed using one or more cameras 42 which are spaced apart from the pattern projector 41 so as to provide such different perspectives, e.g., triangulation perspective. In some embodiments, the pattern projector 41 is configured to project a structured light grid pattern including many lines at once as this allows the simultaneous acquisition of a multitude of samples on an increased area. In these embodiments, it may be convenient to use a pattern of parallel lines. However, other variants of structured light projection can be used in some other embodiments.

The structured light grid pattern can be projected onto the surface to track using the pattern projector 41. In some embodiments, the structured light grid pattern can be produced by incoherent light projection, e.g., using a digital video projector, wherein the patterns are typically generated by propagating light through a digital light modulator. Examples of digital light projection technologies include transmissive liquid crystal, reflective liquid crystal on silicon (LCOS) and digital light processing (DLP) modulators. In these embodiments, the resolution of the structured light grid pattern can be limited by the size of the emitting pixels of the digital projector. Moreover, patterns generated by such digital display projectors may have small discontinuities due to the pixel boundaries in the projector. However, these discontinuities are generally sufficiently small that they are insignificant in the presence of a slight defocus. In some other embodiments, the structured light grid pattern can be produced by laser interference. For instance, in such embodiments, two or more laser beams can be interfered with one another to produce the structured light grid pattern wherein different pattern sizes can be obtained by changing the relative angle between the laser beams.

The pattern projector 41 may emit light that is inside or outside the visible region of the electromagnetic spectrum. For instance, in some embodiments, the emitted light can be in the ultraviolet region and/or the infrared region of the electromagnetic spectrum such as to be imperceptible to the eyes of the medical personnel. In these embodiments, however, the medical personnel may be required to wear protective glasses to protect their eyes from such invisible radiations. As alternatives to structured light, the tracking device 40 may also operate with laser rangefinder technology or triangulation, as a few examples among others.

The tracking device 40 further includes cameras 42 to acquire backscatter images of the illuminated portion of objects. Hence, the cameras 42 capture the pattern projected onto the portions of the object. The cameras 42 are adapted to detect radiations in a region of the electromagnetic spectrum that corresponds to that of the patterns generated by the light projector 41. As described hereinafter, the known light pattern characteristics and known orientation of the pattern projector 41 relative to the cameras 42, are used by the tracking controller 60 to generate a 3D geometry of the illuminated portions, using the backscatter images captured by the camera(s) 42. Although a single camera spaced form the pattern projector 41 can be used, using more than one camera may increase the field of view and increase surface coverage. For instance, in the illustrated embodiment, a pair of cameras 42 is used.

The tracking device 40 may also have one or more filters 46 (hereinafter "the filter 46") integrated into either or both of the cameras 42 to filter out predetermined regions or spectral bands of the electromagnetic spectrum.

The filter 46 can be removably or fixedly mounted in front of any given camera 42. For example, the filter 46 can be slidably movable into and out of the optical path of the cameras 42, manually or in an automated fashion (e.g., using a motor or a solenoid). In some other embodiments, multiple filters may be periodically positioned in front of a given camera in order to acquire spectrally resolved images with different spectral ranges at different moments in time, thereby providing time dependent spectral multiplexing. Such an embodiment may be achieved, for example, by positioning the multiple filters in a filter wheel that is controllably rotated to bring each filter in the filter wheel into the optical path of the given one of the camera 42 in a sequential manner.

In some embodiments, the filter 46 can allow transmittance of only some predetermined spectral features of objects within the field of view, captured either simultaneously by the tracking device 40 or separately by the secondary tracking device 70, so as to serve as additional features that can be extracted to improve accuracy and speed of registration.

More specifically, the filter 46 can be used to provide a maximum contrast between different materials which can improve the imaging process and more specifically the soft tissue identification process. For example, in some embodiments, the filter 46 can be used to filter out bands that are common to backscattered radiation from typical soft tissue items, the surgical structure of interest, and the surgical tool(s) such that backscattered radiation of high contrast between soft tissue items, surgical structure and surgical tools can be acquired. Additionally, or alternatively, where white light illumination is used, the filter 46 can includes band pass filters configured to let pass only some spectral bands of interest. For instance, the filter 46 can be configured to let pass spectral bands associated with backscattering or reflection caused by the bones, the soft tissue and/or markers 71A-D while filtering out spectral bands associated with specifically colored items such as tools, gloves and the like within the surgical field of view. Other methods for achieving spectrally selective detection, including employing spectrally narrow emitters, spectrally filtering a broadband emitter, and/or spectrally filtering a broadband imaging detector (e.g., the camera 12), can also be used. Another light source 48 may also be provided on the tracking device 40, for a secondary tracking option, as detailed below. It is considered to apply distinctive coatings on the parts to be tracked, such as the bone and the tool, to increase their contrast relative to the surrounding soft tissue.

In accordance with another embodiment, the tracking device 40 may include a 3D camera to perform range imaging, and hence determine position data from the captured images during tracking. The expression 3D camera is used to describe the camera's capability of providing range data for the objects in the image it captures, but the 3D camera may or may not produce 3D renderings of the objects it captures. In contrast to structured light 3D imaging, range tracking does not seek specific illumination patterns in distance calculations, but relies instead on the images themselves and the 3D camera's capacity to determine the distance of points of objects in the images. Stated differently, the 3D camera for ranging performs non-structured light ranging, and the expression "ranging" is used herein to designate such non-structured light ranging. Such range tracking requires that the 3D camera be calibrated to achieve suitable precision and accuracy of tracking. In order to be calibrated, the tracking device 40 may use a known visual pattern in a calibration performed in situ, at the start of the tracking, and optionally updated punctually or continuously throughout the tracking. The calibration is necessary to update the camera acquisition parameters due to possible lens distortion (e.g., radial, rotational distortion), and hence to rectify image distortion to ensure the range accuracy.

Figure 4:
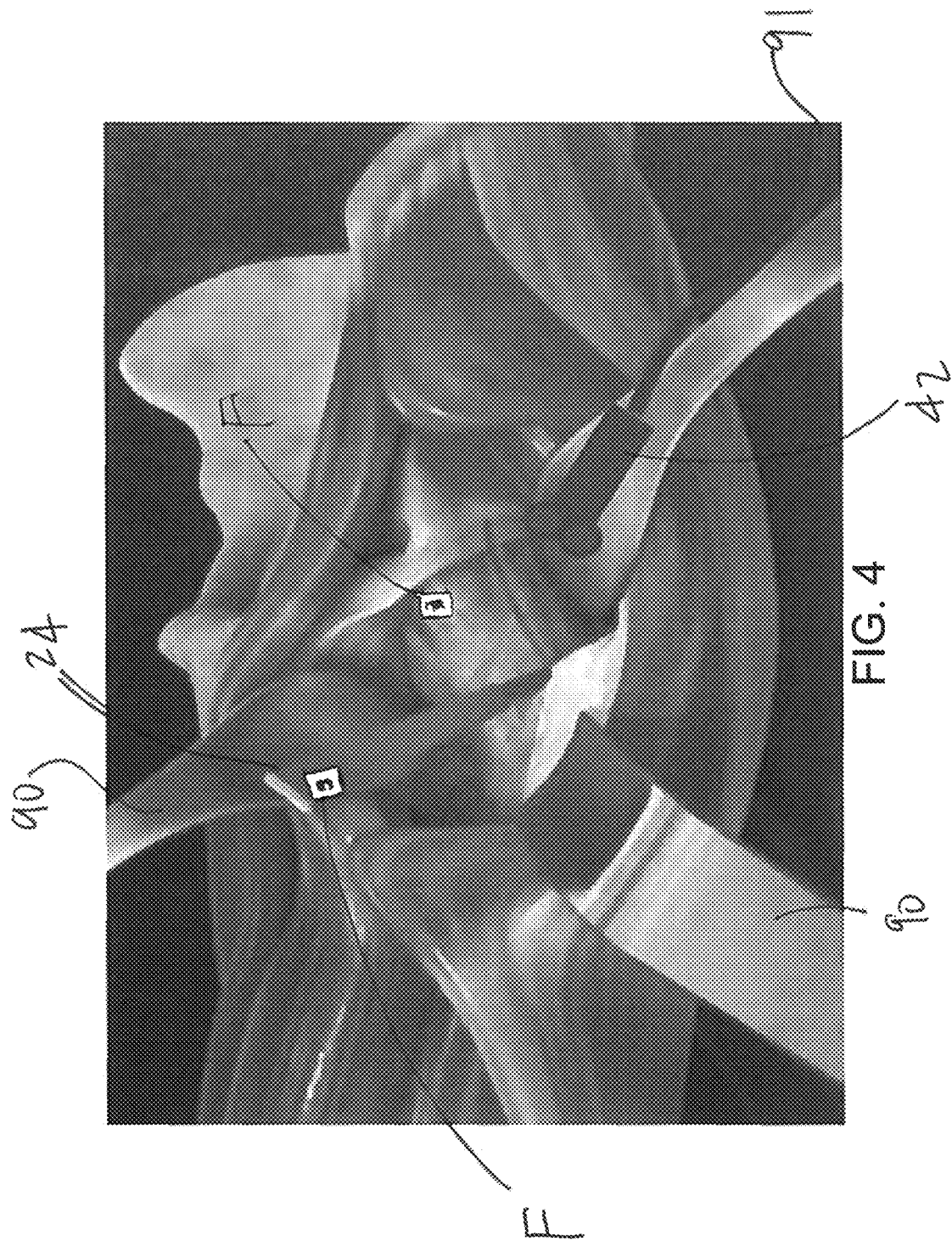
FIG. 4 is a perspective view of a tracking camera on a retractor in accordance with the present disclosure.

Therefore, the tracking device 40 with ranging camera may have a similar configuration as that of FIG. 1, although it may also be smaller, as shown in FIG. 4, in which the tracking device is a 3D camera 42 (as opposed to structured light 3D imaging system). Alternatively, the tracking device 40 may be provided with other equipment, for example for endoscopic tracking. The tracking device 40 may thus be equipped with application-specific lenses, such as a borescopic lens. In the tracking device 40 with ranging camera, component 41 may be a light projector or light source to project light on the target area, if necessary. For example, the tracking device 40 used in endoscopic uses may require its light source. Moreover, the light source may emit light within a given wavelength, including within a non-visible range, such as infrared. The tracking device 40 may feature one or more 3D cameras 42. Filters 46 may also be used to provide a maximum contrast between different materials which can improve the imaging process and more specifically the soft tissue identification process, in a manner similar than as described above.

Figure 2:
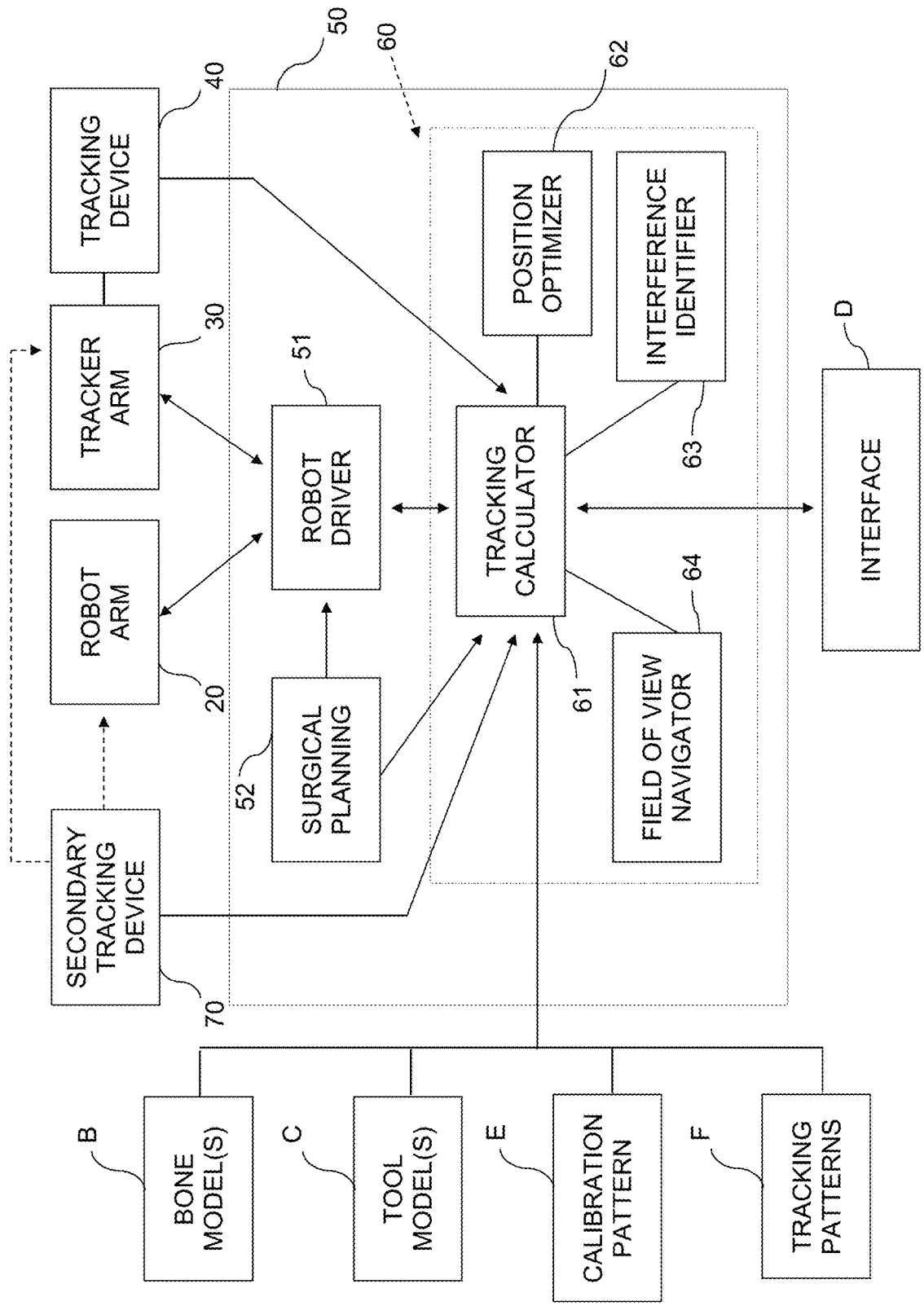
FIG. 2 is a block diagram of a CAS controller and tracking controller with the automated robotic CAS system of FIG. 1.

Referring to FIG. 2, the CAS controller 50 is shown in greater detail relative to the other components of the robotized CAS system 10. The CAS controller 50 has a processor unit to control movement of the robot arm 20, and of the tracker arm 30. The robotized surgery controller 50 provides computer-assisted surgery guidance to an operator through an automated alteration or resection of bones, for instance in the form of surgical data updated during the surgical procedure. The CAS system 10 may comprise various types of interfaces D, for the information to be provided to the operator. The interfaces D may be monitors and/or screens including wireless portable devices (e.g., phones, tablets), audio guidance, LED displays, among many other possibilities. For example, the interface D comprises a graphic user interface (GUI) operated by the system 10. The interface D may also display images captured by the cameras 40 and/or 70, for instance to be used in the collaborative/cooperative control mode of the system 10, or for visual supervision by the operator of the system 10, with augmented reality for example. The CAS controller 50 may drive the robot arm 20 in performing the surgical procedure based on the surgery planning achieved pre-operatively, and controls the tracker arm 30 in suitably orienting and positioning the tracking device 40 to continuously track the tool 24 relative to the anatomical features such as the bones. The CAS controller 50 runs various modules, in the form of algorithms, code, non-transient executable instructions, etc, in order to operate the CAS system 10 in the manner described herein. The CAS controller 50 may be part of any suitable processor unit, such as a personal computer or computers including laptops and desktops, tablets, server, etc.

The controller 50 may hence have a robot driver module 51. The robot driver module 51 is tasked with powering or controlling the various joints of the robot arm 20 and of the tracker arm 30 based on operator demands or on surgery planning. As shown with bi-directional arrows in FIG. 2, there may be some force feedback provided by the robot arm 20 and tracker arm 30 to avoid damaging the bones, and to detect contact between tool head 24, tracked device 40, and anatomical features.

The robot driver module 51 may perform actions based on a surgery planning 52. The surgery planning 52 may be a module programmed specifically for any given patient, according to the parameters of surgery desired by an operator such as an engineer and/or surgeon. The parameters may include geometry of selected, planned bone cuts, planned cut depths, sequence or workflow of alterations with a sequence of surgical steps and tools, tools used, etc.

The tracking controller 60 may be a subpart of the CAS controller 50, or an independent module or system. The tracking controller 60 receives from the tracking device 40 the backscatter images of the objects. The tracking controller 60 processes the backscatter images to determine the relative position of the objects, and segment the objects from the backscatter images. Accordingly, the tracking processor 60 is provided with models of the objects to be tracked. For example, the tracking controller 60 may track bones and tools, and hence uses virtual bone models B and tool models C. The bone models B may be acquired from pre-operative imaging (e.g., MRI, CT-scans), for example in 3D or in multiple 2D views, including with 2D X-ray to 3D bone model technologies. The virtual bone models B may also include some image processing done preoperatively, for example to remove soft tissue or refine the surfaces that will be exposed and tracked. The virtual bone models B may be of greater resolution at the parts of the bone that will be tracked during surgery, such as the knee articulation in knee surgery. The bone models B may also carry additional orientation data, such as various axes (e.g., longitudinal axis, mechanical axis, etc). The bone models B may therefore be patient specific. It is also considered to obtain bone models from a bone model library, with the data obtained from the backscatter images used to match a generated 3D surface of the bone with a bone from the bone atlas. The virtual tool models C may be provided by the tool manufacturer, or may also be generated in any appropriate way so as to be a virtual 3D representation of the tool(s), such as the tool head 24. Additional data may also be available, such as tool orientation (e.g., axis data and geometry). It is considered to provide specific detectable landmarks on the tool(s) to ensure the detectable landmarks will be properly imaged and detected by the tracking controller 60. In matching the 3D geometry to the bone models B, the tracking calculator 61 may reduce its computation using different strategies. According to one possibility, the surgical planning 52 may provide some guidance as to parts of the bones that are altered during the surgical procedure. Likewise, the bone model(s) B may have higher resolution for the parts of the bone that will be altered during surgery. The remainder of the bone may be limited to information on landmarks, such as axis orientation, center of rotation, midpoints, etc. A similar approach may be taken for the tool models C, with the focus and higher detail resolution being on parts of the tools that come into contact with the bone, such as the tool head 24.

In an embodiment with structured light projection, the tracking controller 60 receives the backscatter images from the camera(s) 42, as a result of the structured light projection from the projector 41. In another embodiment, the tracking controller 60 receives the images from the ranging camera 42, and ensures that the ranging camera 42 is calibrated for ranging to be done from the acquired images. An initial calibration may be done using calibration pattern E. The calibration pattern E is placed in the light of sight of the camera 42 such that it is imaged by the ranging camera 42. The calibration pattern E is any appropriate shape and configuration, but may be a planar recognizable pattern with high contrast. The tracking controller 60 has a tracking calculator module 61 that stores a virtual version of the calibration pattern E, including precise geometrical data of the calibration pattern E. The tracking calculator module 61 therefore performs a correspondence between imaged and virtual calibration patterns E. The correspondence may entail calculating the mapping function between landmarks on the planar imaged calibration pattern E and the virtual calibration pattern E. This may include a projection of the calibration patterns E on one another to determine the distortion characteristics of the images of the ranging camera 42, until the rectification values are determined by the tracking calculator module 61 to correct the images of ranging camera 42. This calibration may be repeated punctually through the procedure, for instance based on the camera updating requirements. It may require that the camera 42 is used in conjunction with a calibration reflective surface whose position and orientation relative to the camera 42 is known. The calibration may be automatically performed by the CAS system 10.

The tracking controller 60 may therefore generate a 3D geometry from the backscatter images, using the known patterns of structured light, or calibrated camera images, along with the known shape of the virtual bone model(s) B and/or tool model(s) C. Moreover, the generated 3D geometry may be located in the X, Y, Z, coordinate system using the known positional relation between the pattern projector 41 and the camera(s) 42, in the case of structured light tracking, or the location of the camera 42 in ranging. Therefore, as a first step, the tracking calculator module 61 of the tracking controller 60 generates a 3D geometry of the portions of the object being illuminated. Then, using the virtual models B and/or C of the bone(s) and tool(s), respectively, the tracking controller 60 can match the 3D geometry with the virtual models B and C, with the objects detected being segmented. Consequently, the tracking controller 60 determines a spatial relationship between the objects being illuminated and the preoperative 3D models, to provide a dynamic (e.g. real time or quasi real time) intraoperative tracking of the bones relative to the tools. In an embodiment, the tracking calculator module 61 only determines the position and orientation of the bone in the coordinate system, and locates the tool using other methods, such as obtaining the position and orientation of the tool from the robot driver 51 using the encoders in the robot arm 20. In an embodiment, the position and orientation of the surgical tool 24 calculated by the tracking controller 60 may be redundant over the tracking data provided by the robot driver 51 and robot arm sensors. However, the redundancy may assist in ensuring the accuracy of the tracking of the surgical tool. For example, the redundancy is used as a safeguard against incorrect tracking from the CAS controller 50, for instance due to bone movement or relative movement between the robot arm 20 and the patient and/or table. The redundancy may also allow the reduction of frequency of image processing for the surgical tool 24. Also, the tracking of the tool 24 using the tracking device 40 may be used to detect any discrepancy between a calculated position and orientation of the surgical tool 24 through the sensors on the robot arm 20, and the actual position and orientation of the surgical tool 24. For example, an improper mount of the tool 24 into the chuck of the robot arm 20 could be detected from the output of the tracking device 40, when verified with the position and orientation from the robot driver 51 (e.g., obtained from the encoders on the robot arm 20 or from the secondary tracking device 70). The operator may be prompted to verify the mount, via the interface D.

The tracking controller 60 may also use tracking patterns F to further assist in the tracking of tools and bones, in the case of ranging cameras. The tracking patterns F may or may not have reflective properties, and their tracking may operate with backscatter. More particularly, as shown concurrently in FIGS. 2 and 4, the tracking patterns F may be on patches, plates, chips, affixed to the objects to be tracked. In an embodiment, tracking patterns F may be affixed to multiple bones of an articulation of the patient, such as the tibia and the femur. Once the spatial relationship between images and 3D models of bones and tools has been established for dynamic intraoperative tracking of the bones relative to the tools, the tracking device 40 and the tracking controller 60 may rely on the optical images of the tracking patterns F for the dynamic intraoperative tracking. The position and orientation of the tracking patterns F relative to their respective bones/tools is recorded as part of the spatial relationship by the tracking calculator module 61. As the tracking patterns F are contrasting recognizable patterns, they may be more easily definable as observed by the camera 42 than low contrast uniform items, such as a bone surface. The tracking patterns F could be made from or coated with non-stick material to prevent blood, bodily fluids or particulate matter from obscuring the pattern. Therefore, using optical detection, the tracking calculator module 61 uses the spatial relationship between the tracking patterns F and respective bone/tool for subsequent tracking. The spatial relationship may be established in situ, or may be preprogrammed as well, especially for tools configured to receive the tracking patterns F in a predetermined way. The tracking patterns F could be made from bio-resorbable material such that they do not need to be removed prior to closing the incision. The tracking patterns F may each have a unique pattern that has a single orientation (e.g., no axis of symmetry), so as to have their orientation trackable. It is contemplated as well to have tracking patterns F with the same pattern, for example with steps performed to associate bone(s) and/or tool(s) to each tracking pattern F. In an embodiment, the tracking patterns F are used in complementary fashion to the bone/tool structured light tracking described above, for example as taking over for the structured light tracking, or to validate the structured light tracking. In another embodiment, the tracking patterns F are used with the position data from the robot arm 20 for the tracking. The tracking patterns F may be in the form of a high resolution dark pattern on a light background, or vice versa, similar to a QR code, to a bar code, etc. In an embodiment, the patterns F are on a flat surface, and thus are two-dimensional (2D). The tracking patterns F may be less than 1.0 inch in diameter, or less than 1.0 inch in width and/or in height. The tracking patterns F may be adhered, tacked, nailed, etc to the bone and/or to the tool.

The tracking device 40 may continuously capture backscatter images, for the tracking controller 60 to perform a continuous tracking of the objects. The frequency of capture may vary according to different factors. For example, there may be different phases during the surgical workflow, some in which the tracking requires a more dynamic update, and some in which tracking updates are less important. Another factor that may affect the image capture frequency is the fixed relation of the objects. For example, once the tracking controller 60 identifies a bone from the backscatter images, the frequency capture by the tracking device 40 may be reduced if the bone is fixed (e.g., by the foot support A1 or tight support A2 of FIG. 1), if the bone alterations have not yet begun. Also, when both a tool head 24 and a bone are tracked, the frequency capture may be reduced when the tool head 24 and the bone are spaced from one another by a given distance, and increased as the proximity between the tool head 24 and the bone is increased. The tracking calculator module 61 may drive the tracking device 40 in order to control the frequency. For example, the tracking calculator module 61 may adapt the frequency using the surgical planning 51, e.g., anticipating upcoming steps in the workflow, etc. The tracking calculator module 61 may consequently toggle between a low-frequency capture mode and a high-frequency capture mode, for example. The low-frequency capture mode may be in instances in which the tool head 24 is at a given distance from the bone, and is not driven to alter the bone. The low-frequency capture mode may also be operated when the objects are in a fixed relation relative to one another. Other modes are contemplated.

The tracking device 40 is on the tracker arm 30 for its position and orientation to be adjusted to ensure it provides suitable backscatter images of the relevant objects throughout the surgical procedure, or at least during navigation steps, if necessary. The tracking controller 60 is therefore tasked with ensuring that the tracking device 40 is in a suitable position and orientation as a function of the surgical workflow, and controls an automated robotized variation of the position and orientation of the tracking device 40 (e.g., by moving the tracking device 40, the bone, etc). For this purpose, the tracking controller 60 may have different modules to assist the tracking calculator module 61 in determining a desired position and orientation of the tracking device 40, for the tracker arm 30 to be driven by the robot driver module 51 into reaching that desired position and orientation.

According to one embodiment, the tracking controller 60 has a position optimizer module 62. The position optimizer module 62 may identify situations when the backscatter images captured by the tracking device 40 feature excessive environment in contrast to the objects to be tracked (e.g., bone(s) and tool(s)), i.e., the ratio of tracked object for environment is not sufficiently high. For example, if the proportion of pixels in the backscatter images identified as being bone or tool is below a given threshold, the position optimizer module 62 may indicate to the tracking calculator module 61 that the tracking device 40 must be realigned, or recentered. As the position optimizer module 62 performs the image analysis to identify the target zones in the backscatter images, it may suggest suitable position and orientation for the tracking device 40 to increase the proportion of the tracked objects in the images. The position optimizer module 62 may for example isolate soft tissue from bone matter in the backscatter images. In some embodiments, the position optimizer module 62 discriminates between soft tissue and bone matter in the backscatter images based on the spectral band of the backscattered light. For instance, light backscattered in a first spectral band can be associated to soft tissue whereas light backscattered in a second spectral band can be associated to bone matter. Accordingly, the position optimizer module 62 can suggest suitable position and orientation for the tracking device 40 to increase the proportion of backscattered light in one of the first and second spectral bands, depending on which one of the soft tissue and the bone matter is tracked. The action of the position optimizer module 62 may cause a dynamic adjustment of the position and orientation for the tracking device 40 during surgery.

The tracking controller 60 may have an interference identifier module 63. The interference identifier module 63 may detect when interference occurs in the line of sight between the tracking device 40 and the tracked objects. The interference may be of temporary nature, such as the presence of an interfering object in the line of sight, or may be of permanent nature, such as soft tissue on the bone (e.g., cartilage, not part of the virtual bone model B). The interference identifier module 63 may determine the nature of the interference. For example, the interference identifier module 63 may detect the appearance of an object from a continuous tracking of the 3D geometry by the tracking calculator module 61. The interference identifier module 63 may also detect a discrepancy between the virtual bone model B and the 3D geometry. If the discrepancy has backscattering properties different than those of the surrounding surfaces, the interference identifier module 63 may identify the nature of the interference, such as cartilage or bodily fluids. For instance, the backscattering properties of the discrepancy may belong to a given spectral band which is known to be associated with soft tissue rather than bone matter. As a result of the identification of interference by the interference identifier module 63, the tracking controller 60 may ignore some types of interferences to proceed with the continuous tracking, may suggest a repositioning of the tracking device 40 to an interference-less position and orientation or a position and orientation with a reduction thereof, and/or signal an interference to the operator of the CAS system 10 via the interface D.

The tracking controller 60 may also have a field-of-view (FOV) navigator module 64. The FOV navigator module 64 may perform with the tracking calculator module 61 a global field of view scan of the surgical site in the early stages of the surgical workflow, and store same, for subsequent reference by the tracking controller 60. This global FOV scan may be particularly useful when the bones are fixed (e.g., with the foot support A1 and the thigh support A2). The FOV navigator module 64 may therefore store a correlation between the location of the tracking device 40 and the location of the objects in the coordinate system. As a function of the surgical planning 52, the tracking controller 60 may determine a suitable position and orientation for the tracking device 40 in anticipation of interventions of tools on the bone. The tracking controller 60 may know that the tool will be oriented and positioned in a given manner in the coordinate system relative to the bone according to the next upcoming step of the surgical planning 52, and may rely on the FOV navigator module 64 to suggest a suitable position and orientation based on the FOV scan data.

Therefore, the tracking controller 60 continuously updates the position and/or orientation of the patient bones and tools in the coordinate system using the data from the tracking device 40, and may ensure that the tracking is continuously updated by acting concurrently with the robot driver module 51 to adjust the position and/or orientation of the tracking device 40. Moreover, once alterations are done, the tracking performed by the tracking controller 60 may be used to validate bone alterations, such as cut planes. In such a case, the surgical planning 52 provides the planned alterations in the model of the bone. The structured light technology can determine the location of a cut plane relative to a remainder of the bone, and thus the tracking controller 60 may determine of the cut plane is located according to planning, or if a discrepancy is present. The tracking controller 60 may perform other functions as well, such as selectively dimming or shutting off lights in the operating room if excessive glare interfering with the tracking device 40 is detected. The tracking controller 60 may hence be interfaced to the lighting system of the operating room in an embodiment, for instance with appropriate wireless protocols. The tracking controller 60 may also send instructions via the interface D to request adjustments to the ambient lighting system.

The surgical planning 52 may incorporate a navigation file for robotized surgery to calibrate the robot arm 20 and the tracking device 40 on the tracker arm 30 prior to commencing surgery. For example, the calibration subfile may include the virtual bone model B of the patient, for surface matching to be performed by a registration pointer of the robot arm 20, used for contacting the bone. The robot arm 30 would obtain a cloud of bone landmarks of the exposed bones, to reproduce a 3D surface of the bone. The 3D surface would then be matched to the bone model B of the patient, to set the 3D model in the X, Y, Z coordinate system, in combination with concurrent optical tracking as described above. An operator's assistance may be requested initially, for instance to identify tracked landmarks and focus the tracking device 40. This may be part of the calibration subfile. The calibration pattern E and the tracking patterns F may also be part of the calibration subfile, if the tracking device 40 is a non-structured light ranging camera.

Referring back to FIG. 1, the secondary tracking device 70 may optionally be used to supplement the tracking done by the tracking device 40. For example, the secondary tracking device 70 may assist in providing additional accuracy in relating the position and orientation of the tool head 24 to that of the tracking device 40, in the X, Y, Z coordinate system. According to an embodiment, the secondary tracking device 70 comprises a camera that optically sees and recognizes retro-reflective markers 71A, 71B, 71C and/or 71D, with 71B and 71C optionally used to track the limbs in six DOFs, namely in position and orientation. The marker 71A is on the tool head 24 of the robot arm 20 such that its tracking allows the controller 50 to calculate the position and/or orientation of the tool head 24 and tool 26A thereon. Likewise, marker 71D is on the tracking device 40 at the end of the tracker arm 30 such that its tracking allows the controller 50 to calculate the position and/or orientation of the tracking device 40. Markers 71B and 71C are fixed to the patient bones, such as the tibia for marker 71B and the femur for marker 71C. As shown, the markers 71B and 71C attached to the patient need not be invasively anchored to the bone, as straps or like attachment means may provide sufficient grasping to prevent movement between the markers 71B and 71C and the bones, in spite of being attached to soft tissue. However, the references 71B and 71C could also be secured directly to the bones.

The markers 71A-D can be provided in the form of retro-reflective markers or in the form of active emitters. In both cases, the filter 46 of the tracking device 40 is designed so as to let pass spectral bands associated with the light reflected or emitted by the markers 71A-D such as to be detectable by the camera(s) 42, if it is intended for the tracking device 40 to use these markers 71A-D. However, it may be desired to use filters to block light reflected by the markers 71A-D to avoid interference with the operation of the tracking device 40 and thus with the backscatter and structured light, in an embodiment in which the tracking device 40 and secondary tracking device 70 are used independently from one another.

In the illustrated embodiment, the markers 71A-D are retro-reflective markers. Accordingly, the light source 48 is provided to illuminate the markers 71A-D during the surgery. The light source 48 is adapted to emit light which will be reflected by the retro-reflective markers 71A-D. For instance, if the markers 71A-D are passively reflecting markers, the light source 48 is chosen to exhibit a spectral profile to be transmitted through the filter 46. Alternatively, if the markers 71A-D are fluorescent markers, the light source 48 is selected to have a spectral profile suitable for generating fluorescence from the markers 71A-D, and the filter 46 includes a spectral pass band for transmitting the emitted fluorescence. One example of such markers includes passive infrared (IR) markers which are specifically designed to reflect light in the infrared portion of the electromagnetic spectrum, in which case the light source 48 is an IR light source. In the embodiment illustrated in FIG. 1, the light source 48 is made integral to the tracking device 40. However, in other embodiments, the light source 48 can be separate from the tracking device 40.

As an alternative to optical tracking, the secondary tracking system 70 may consist of inertial sensors (e.g., accelerometers, gyroscopes, etc) that produce tracking data to be used by the tracking controller 60 to assist in continuously updating the position and/or orientation of the robot arm 20. Other types of tracking technology may also be used. While the secondary tracking system 70 may be present to assist in ensuring the accuracy of the CAS system 10, the system 10 may also rely solely on the combination of the tracking device 40 and the sensors on the robot arm 20 and the tracker arm 30 (e.g., encoders, etc) throughout the surgical procedure. The combination of the tracking device 40 and the sensors on the robot arm 20 and the tracker arm 30 may provide redundant tracking data ensuring that the surgical procedure meets the required precision and accuracy.

Figure 3:
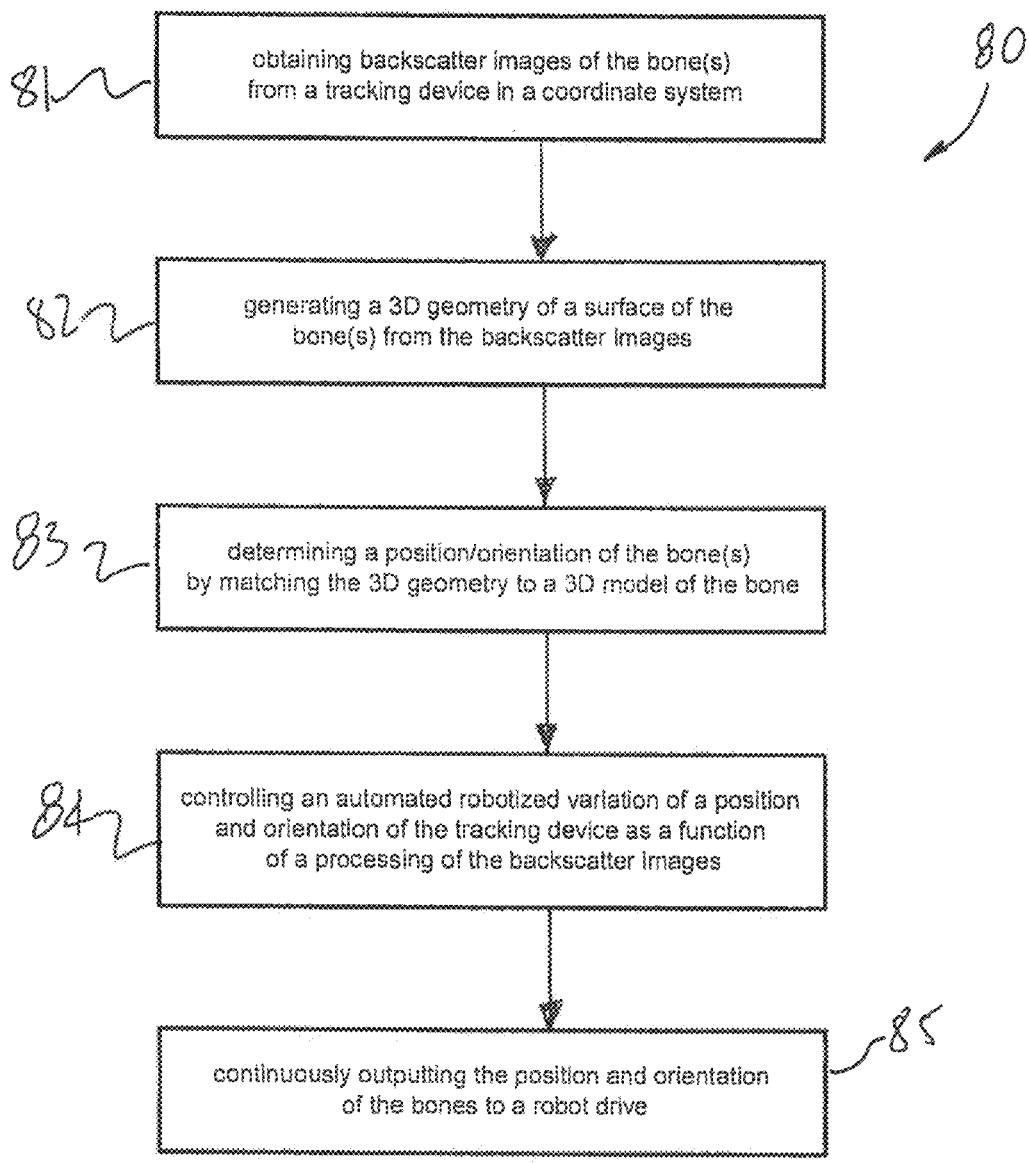
FIG. 3 is a flow diagram of a method for tracking objects in robotized computer-assisted surgery.

Referring to FIG. 3, a method for tracking one or more bones and objects such as tools, in robotized computer-assisted surgery, is generally shown at 80. The method may be performed for instance by one or more processors related to the CAS controller 50 and/or the tracking controller 60 (which may also be referred to as system), and operating jointly with the robot driver 51. The method may be inscribed on a non-transitory computer-readable memory communicatively coupled to the processing unit of the CAS controller 50 and/or the tracking controller 60, for example in the form of computer-readable program instructions executable by the processing unit. According to 81, backscatter images of one or more bones are obtained, from a tracking device such as the tracking device 40, in the coordinate system. This may include obtaining images of objects other than the bone, such as surgical tools. It may also include projecting structured light patterns on the objects to track. The backscatter images may be used to calibrate the ranging camera 42, for non-structured light ranging, along with the calibration pattern E.

According to 82, a three-dimensional geometry of a surface of the bone(s) is generated from the backscatter images, the three-dimensional geometry of the surface being in the coordinate system. This may include generating a three-dimensional geometry of a surface of the surgical tool from the backscatter images in the coordinate system.

According to 83, a position and orientation of the bone(s) is determined in the coordinate system by matching the three-dimensional geometry of the surface of the at least one bone to a three-dimensional model of the bone. The position and orientation of the surgical tool may also be determined in the coordinate system by matching the three-dimensional geometry of the surface of the surgical tool to a three-dimensional model of the surgical tool. A position and orientation of tracking patterns F on the bone and/or tool may also be determined in the coordinate system for subsequent dynamic tracking.

According to 84, an automated robotized variation of the position and/or orientation of the tracking device 40 is controlled, as a function of a processing of the backscatter images, for example to ensure continuous field of view or to improve the tracking resolution. The controlling of the automated robotized variation may comprise identifying an image ratio of the bone in the backscatter images and controlling the automated robotized variation to increase the image ratio. The controlling of the automated robotized variation may comprises creating field of view data indicative of the orientation of the bone(s) as a function of the position and orientation of the tracking device 40, and selecting the position and orientation of the tracking device 40 as a function of a desired point of view, i.e., relative orientation, of the bone by the tracking device 40. The selection of the position and orientation of the tracking device 40 as a function of a desired point of view of the at least bone may include determining from surgery planning a location of a robotized tool altering the bone.

According to 85, the position and orientation of the bone(s) in the coordinate system is continuously output to the robot driver 51 controlling the robot arm 20 supporting the surgical tool 24 in the coordinate system for altering the bone. The position and orientation of the bone(s) in the coordinate system may be continuously output with the position and orientation of the surgical tool in the coordinate system. The continuous output may include imaging of bone alterations, such as cut planes, for such bone alterations to be validated in comparison to surgical planning 52.

Referring to FIG. 4, the non-structured light 3D camera 42 is shown, as being mounted directly to a tool, in this case to one of the retractors 90. The retractors 90 are in close proximity to the operation site, and are generally immovable during the surgical procedure, whereby they form an efficient base for receiving the camera 42. This arrangement may also be used with the structured light head described above. It is hence contemplated to mount the camera 42 directly to some tools. For instance, the camera 42 may be mounted directly to a drill head, etc, as it may often have a direct line of sight between the tool and the target site on the bone surface. Other examples include an endoscope, registration pointer, cutting tools, reamers, etc. The tracking for the arrangement of FIG. 4 may depend on the context. If the camera 42 has a direct and non-obstructed line of sight with the tool and target site, its position and orientation is not relevant. This applies to robotic and non-robotic applications. If it is mounted to a robotic arm, as in FIG. 1, the various tracking systems described above may be used. It is also contemplated to provide an optic fiber with Braggs network 91 to determine the position and orientation of the camera 42. It is also contemplated to provide tracking patterns F on implants as well, for instance as integrated thereon, for precise validation of implant placement.

While the description refers to the robot arm 20 as having a tool head 24 and the tracker arm 30 as having the tracking device 40, it may be possible to swap the tool head 24 and the tracking device 40. This may be done for optimal placement of the tool head 24. For example, some types of procedures may benefit from such a swap, such as a bilateral total knee arthroplasty when the operation moves from one leg to the next. The present disclosure refers to the system 10 has performing continuous tracking. This means that the tracking may be performed continuously during discrete time periods of a surgical procedure. Continuous tracking may entail pauses, for example when the bone is not being altered. However, when tracking is required, the system 10 may provide a continuous tracking output, with any disruption in the tracking output triggering an alarm or message to an operator.

The invention claimed is:

1. A system for tracking at least one bone in robotized computer-assisted surgery, comprising:
   a tracking device on a robotized tracker arm;
   a robot arm supporting a surgical tool;
   a processing unit; and
   a non-transitory computer-readable memory communicatively coupled to the processing unit and comprising computer-readable program instructions executable by the processing unit for:
   obtaining backscatter images of the at least one bone from a tracking device in a coordinate system;
   generating a three-dimensional geometry of a surface of the at least one bone from the backscatter images, the three-dimensional geometry of the surface being in the coordinate system;
   determining a position and orientation of the at least one bone in the coordinate system by matching the three-dimensional geometry of the surface of the at least one bone to a three-dimensional model of the bone;

controlling an automated robotized variation of at least one of a position and orientation of the tracking device on the robotized tracker arm as a function of a processing of the backscatter images; and continuously outputting the position and orientation of the at least one bone in the coordinate system to a robot driver controlling the robot arm supporting the surgical tool in the coordinate system for altering the bone.

2. The method according to claim 1, wherein controlling the automated robotized variation comprises identifying an image ratio of the at least one bone relative to environment in the backscatter images and controlling the automated robotized variation to increase the image ratio.

3. The system according to claim 1, wherein controlling the automated robotized variation comprises creating field of view data indicative of the orientation of the at least one bone relative to the position and orientation of the tracking device, and selecting the position and orientation of the tracking device as a function of a desired point of view of the at least one bone.

4. The system according to claim 3, wherein selecting the position and orientation of the tracking device as a function of a desired point of view of the at least bone includes determining an upcoming location of the surgical tool on the robot arm from a surgical flow of surgery planning.

5. The system according to claim 1, wherein:
obtaining backscatter images of the at least one bone from the tracking device in the coordinate system comprises obtaining backscatter images of the surgical tool; and
generating the three-dimensional geometry of the surface of the at least one bone from the backscatter images comprises generating a three-dimensional geometry of a surface of the surgical tool from the backscatter images in the coordinate system.

6. The system according claim 5, wherein continuously outputting the position and orientation of the at least one bone in the coordinate system includes continuously outputting the position and orientation of the surgical tool to the robot driver controlling the robot arm supporting the surgical tool in the coordinate system.

7. The system according to claim 6, further comprising verifying the position and orientation of the surgical tool obtained from the backscatter images with a position and orientation of the surgical tool provided by the robot driver and outputting a discrepancy.

8. The system according to claim 5, wherein determining the position and orientation of the at least one bone in the coordinate system includes determining the position and orientation of the surgical tool in the coordinate system by matching the three-dimensional geometry of the surface of the surgical tool to a three-dimensional model of the surgical tool.

9. The system according to claim 1, wherein obtaining backscatter images of the at least one bone from a tracking device in a coordinate system includes obtaining the backscatter images in a first frequency capture mode when the surgical tool is distal to the bone, and in a second frequency capture mode when the surgical tool is proximal to the bone, the second frequency capture mode being greater than the first frequency capture mode.

10. The system according to claim 9, wherein obtaining the backscatter images in the first frequency capture mode or the second frequency capture mode includes determining an upcoming location of the surgical tool on the robot arm from a surgical flow of surgery planning.

11. The system according to claim 1, wherein obtaining the backscatter images of the at least one bone includes obtaining the backscatter images from a point of view on a tool interfacing with an anatomical part surrounding the bone or with the bone.

12. The system according to claim 1, wherein controlling the automated robotized variation of at least one of the position and orientation of the tracking device includes controlling the robotized tracker arm of the tracking device.

13. The system according to claim 1, wherein generating the three-dimensional geometry of the surface of the at least one bone from the backscatter images includes generating the three-dimensional geometry of an altered surface, and wherein determining the position and orientation of the at least one bone in the coordinate system includes determining the position and orientation of the altered surface in the bone.

14. The system according to claim 13, further comprising verifying the position and orientation of altered surface with a position and orientation of a planned altered surface from surgery planning and outputting a discrepancy.

15. The system according to claim 1, further comprising identifying an interference from the backscatter images of the at least one bone and outputting an indication of interference.

16. The system according to claim 1, wherein obtaining the backscatter images includes obtaining the backscatter images from visible structured light.

17. A system for tracking at least one bone in robotized computer-assisted surgery, comprising:
a tracking device including at least a structured light source and a camera to generate and obtain the backscatter images, the tracking device being on the robotized tracker arm
a robot arm supporting a surgical tool; and
a computer-assisted surgery controller for
obtaining backscatter images of the at least one bone from the tracking device in a coordinate system,
generating a three-dimensional geometry of a surface of the at least one bone from the backscatter images, the three-dimensional geometry of the surface being in the coordinate system,
determining a position and orientation of the at least one bone in the coordinate system by matching the three-dimensional geometry of the surface of the at least one bone to a three-dimensional model of the bone,
controlling an automated robotized variation of at least one of a position and orientation of the tracking device as a function of a processing of the backscatter images, and
continuously outputting the position and orientation of the at least one bone in the coordinate system to a robot driver controlling the robot arm supporting Hall the surgical tool in the coordinate system for altering the bone.

18. A method for tracking at least one bone in computer-assisted surgery, comprising:
obtaining backscatter images of the at least one bone from a tracking device in a coordinate system, as positioned on a tool interfacing with an anatomical part surrounding the bone or with the bone;

generating a three-dimensional geometry of a surface of the at least one bone from the backscatter images, the three-dimensional geometry of the surface being in the coordinate system;

determining a position and orientation of the at least one bone in the coordinate system by matching the three-dimensional geometry of the surface of the at least one bone to a three-dimensional model of the bone; and continuously outputting the position and orientation of the at least one bone in the coordinate system to an interface for providing guidance in altering the bone.

* * * * *